(12) United States Patent
Paolini et al.

(10) Patent No.: US 9,791,270 B2
(45) Date of Patent: Oct. 17, 2017

(54) METHOD AND SYSTEM FOR DETECTING OR VERIFYING A BLOOD CIRCUIT CONNECTED TO AN EXTRACORPOREAL BLOOD TREATMENT CONSOLE

(75) Inventors: Francesco Paolini, Ganaceto (IT); Paolo Rovatti, Finale Emilia (IT)

(73) Assignee: Gambro Lundia AB, Lund (SE)

( * ) Notice: Subject to any disclaimer, the term of this patent is extended or adjusted under 35 U.S.C. 154(b) by 810 days.

(21) Appl. No.: 13/997,532

(22) PCT Filed: Dec. 21, 2011

(86) PCT No.: PCT/IB2011/003103
§ 371 (c)(1),
(2), (4) Date: Oct. 24, 2013

(87) PCT Pub. No.: WO2012/085644
PCT Pub. Date: Jun. 28, 2012

(65) Prior Publication Data
US 2014/0048460 A1    Feb. 20, 2014

Related U.S. Application Data

(60) Provisional application No. 61/426,214, filed on Dec. 22, 2010.

(30) Foreign Application Priority Data

Dec. 22, 2010  (EP) .................................... 10015918

(51) Int. Cl.
*G01B 13/00*    (2006.01)
*A61M 1/16*    (2006.01)
(Continued)

(52) U.S. Cl.
CPC ............... *G01B 13/00* (2013.01); *A61M 1/16* (2013.01); *A61M 1/3607* (2014.02);
(Continued)

(58) Field of Classification Search
None
See application file for complete search history.

(56) References Cited

U.S. PATENT DOCUMENTS

| 2008/0214981 | A1 | 9/2008 | Delnevo |
| 2010/0114005 | A1 | 5/2010 | Rovatti |
| 2013/0177455 | A1 | 7/2013 | Kamen |

FOREIGN PATENT DOCUMENTS

| IT | WO 2008125894 A1 * | 10/2008 | ............. A61M 1/16 |
| WO | 2006/123197 A1 | 11/2006 | |

(Continued)

*Primary Examiner* — Heidi Kelley
*Assistant Examiner* — Eric McCullough
(74) *Attorney, Agent, or Firm* — K&L Gates LLP (57) ABSTRACT

A method to determine a type of blood circuit attached to an extracorporeal blood treatment console including: pumping a liquid through a blood passage of the blood circuit, sensing a first pressure in: the blood passage while the passage is closed and pumping stopped, pumping an additional amount of the liquid into the blood passage while the blood passage is and remains closed and thereafter sensing a second pressure, and determine a dimensional characteristic of a fluid passage in the blood passage based on the additional amount of the liquid and the second pressure.

20 Claims, 3 Drawing Sheets

(51) Int. Cl.
*A61M 1/34* (2006.01)
*A61M 1/36* (2006.01)

(52) U.S. Cl.
CPC ........ *A61M 1/3609* (2014.02); *A61M 1/3621* (2013.01); *A61M 1/3632* (2014.02); *A61M 1/3644* (2014.02); *A61M 1/3646* (2014.02); *A61M 1/34* (2013.01); *A61M 1/36* (2013.01); *A61M 1/3627* (2013.01); *A61M 1/3643* (2013.01); *A61M 2205/123* (2013.01); *A61M 2205/3331* (2013.01); *A61M 2205/3365* (2013.01); *A61M 2205/3379* (2013.01); *A61M 2205/50* (2013.01); *A61M 2205/502* (2013.01); *A61M 2205/60* (2013.01); *A61M 2205/6018* (2013.01); *A61M 2205/70* (2013.01)

(56) References Cited

FOREIGN PATENT DOCUMENTS

| WO | 2008/125894 A1 | 10/2008 | |
|---|---|---|---|
| WO | 2009/051669 A1 | 4/2009 | |
| WO | WO 2009051669 A1 * | 4/2009 | ............ A61M 1/106 |
| WO | 2009/094183 A1 | 7/2009 | |

\* cited by examiner

METHOD AND SYSTEM FOR DETECTING OR VERIFYING A BLOOD CIRCUIT CONNECTED TO AN EXTRACORPOREAL BLOOD TREATMENT CONSOLE

This application is the U.S. national phase of International Application No. PCT/IB2011/003103 filed 21 Dec. 2011 which designated the U.S. and claims priority to U.S Patent Application Ser. No. 61/426,214 filed 22 Dec. 2010 and European Patent Application No. 10015918.5 filed 22 Dec. 2010, the entire contents of all of which are hereby incorporated by reference.

BACKGROUND OF THE INVENTION

The invention relates to extracorporeal blood treatment systems and particularly to connecting a releasable blood circuit to a blood treatment console. The invention may be applied to determine or verify the type or size of disposable extracorporeal circuit coupled to a blood treatment console.

An extracorporeal blood treatment system may include a blood treatment or blood collection console (referred to herein as a blood treatment console) and a disposable blood circuit that connects to the console. The blood circuit typically includes all or a portion of a blood passage having an access line (such as a flexible plastic tube, conduit or other liquid passage) into which blood is withdrawn from a patient and a return line through which treated blood is infused to the patient. The blood circuit is typically releasably connected to the blood treatment console.

The blood treatment console may be used with various types of blood circuits, such as adult and non-adult, e.g. pediatric, blood circuits. When a blood circuit is attached, the console should be properly configured manually or automatically to operate with the attached blood circuit. The operational settings for the console may depend on the type of blood circuit that is attached. For example, the pump speed for moving blood through the circuit and pressure levels in the circuit may differ for an adult blood circuit and a non-adult, e.g. pediatric blood circuit. Operational settings appropriate for one type of blood circuit may not be appropriate for another type of blood circuit.

The operational settings for a console may be set manually by an operator, such as by nurse or other health care provider. The console may offer the operator a selection of settings and prompt the operator to enter operational settings for a blood treatment to be performed on a patient. The console operator typically presses buttons, soft keys, a touch screen or other input devices on the console to select the operational settings appropriate for the blood circuit and patient. The operator also loads the blood circuit onto the console, such as by connecting blood lines in the circuit to the console. The operator may also connect the blood lines to the patient, such as by connecting the access and return blood lines to catheters or needles inserted in the vascular system of the patient.

The console operators are generally medical professions who are trained in the operation of the blood treatment system, especially in how to select the correct operational settings for the console and the proper the blood circuit. Nevertheless, there is a possibility that the operation settings for one blood circuit may be inadvertently used for a different type of blood circuit.

It is important that the operation settings inputted to or automatically selected by the console correspond to the type of blood circuit connected to the console. For example, when a pediatric blood circuit is connected to the console the operational settings of the console should be for a pediatric patient.

Certain techniques have been published to detect the type of blood circuit attached to a blood treatment console. By way of example, WO 2008/125894 and U.S. Patent Application Publication 2010/0114005 disclose techniques for detecting the type of blood circuit attached to a blood console. An apparatus for controlling an extracorporeal system, including automatically selecting proper console settings, is disclosed in WO 2006/123197. Even with these existing techniques, there remains a need and desire for devices and methods that accurately, simply and quickly detect the type of blood circuit connected to a blood console or verifying that the blood circuit connected to the console corresponds to the operational settings of the console.

BRIEF DESCRIPTION OF THE INVENTION

It is desirable that the blood treatment system automatically selected the proper operational settings upon detecting that a blood circuit has been connected to the console. Alternatively, it is desirable that the blood treatment system automatically verify that settings manually programmed into the console by an operator are proper for the blood circuit attached to the console. It is also desirable that the selection or verification of the blood circuit occur before the blood circuit is coupled to the patient for blood treatment.

An extracorporeal blood treatment system and method have been invented and are disclosed herein which automatically recognizes the type of extracorporeal circuit applied to the console of the system. The system and method disclosed herein may be applied to program the console with the operational settings proper for the type of blood circuit connected to the console. The disclosed system and method may also be applied to verify that operational settings programmed into the console are proper for the type of blood circuit connected to the console.

The disclosed system and method may be applied to detect or verify whether the blood circuit connected to the console is suitable for an adult patient or a pediatric patient. The disclosed system and method may be applied alone or in combination with other systems for detecting or verifying the type of blood circuit attached to a console.

An novel apparatus has been conceived and is disclosed herein including at least one pump and a controller, the pump being connectable to an extracorporeal blood circuit including a blood access or return passage, a blood passage coupled to the pump, wherein the blood passage includes a chamber having an gas filled portion, and the controller: controls the pump to pump a liquid into the blood return or access passage and the blood passage; closes the return or access passage or issues a prompt to close the passage, after the passages are filled with the liquid; receives first pressure data from the pressure sensor while the pump is stopped and the shut-off device connected to the blood passage remains closed; determines a first pressure value based on the first pressure data; while the shut-off device is closed, controls the pump to pump an additional amount of the liquid into the passages; receives second pressure data generated by the pressure sensor while the shut-off device remains closed and the additional amount of the liquid is pumped in the passages; determines a second pressure value based on the second pressure data, and determines a dimensional characteristic of the blood passage based on the second pressure value and the additional amount of the liquid.

The additional amount of the liquid may be determined by a predetermined pumping operation, and the dimensional characteristic of the blood passage may be determined based on a comparison of the first pressure value and the second pressure value. The dimensional characteristic of the blood passage may be alternatively determined based on the additional amount of the fluid pumped to cause the second pressure value to reach a predetermined pressure value. The liquid may be a priming liquid drawn from a source of the priming liquid connectable to the blood passage.

The dimensional characteristic may be a diameter of the blood passage. The blood passage may be a blood tube for withdrawing blood from the patient.

The controller may further cause the console to generate an audible or visual signal indicative of the determined dimensional characteristic. The audible or visual signal may indicate whether the blood passage is for an adult blood circuit or a non-adult blood circuit. The console may display or report a type of the extracorporeal circuit corresponding to the determination of the dimensional characteristic. The controller may verify whether the determined dimensional characteristic is within a predetermined range of dimensional characteristics associated with an operational setting of the console.

The pump may be a peristaltic pump. The predetermine amount of the liquid may be based on pumping the liquid at a predetermined rate and for a predetermined period. The blood treatment device may attach to the console separately from the blood passage. The pressure sensor may be mounted on at least one of the extracorporeal blood treatment console, the blood treatment device, bubble trap and the blood circuit. The apparatus may be a hemodialysis apparatus or an hemo(dia)filtration apparatus. The shut-off device may be a clamp attached to the blood passage.

The controller may include a non-transitory memory and a processor executing program instructions stored in the memory. The program instructions cause the controller to operate the pump, receive pressure data from the pressure sensor and generate displays or reports.

An apparatus for extracorporeal blood treatment has been conceived and is disclosed herein comprising: an extracorporeal blood treatment console including a pump and a controller; a blood circuit including access and return passages and a blood passage, wherein the access passage is adapted to receive blood from a vascular system of a mammalian patient, the blood passage receives blood from the access passage and the return passages coveys treated blood to be infused to the patient, the passages include one or more blood chambers having a gas filled region; a peristaltic pump associated with the extracorporeal blood treatment console, wherein at least one of the blood passages is connected to the pump when the extracorporeal circuit connects to the extracorporeal blood treatment console; a source of priming fluid; a pressure sensor generating pressure data indicative of a pressure in the blood passage; the controller controlling the peristaltic pump and receiving the pressure data, wherein the controller: controls the pump to pump a liquid into the return passage; closes the access passage downstream of the blood chamber or prompts closure of access passage downstream of the blood chamber; receives first pressure data while the pump is stopped and after the closure of the access passage; determines and stores a first pressure value based on the first pressure data; while the shut-off device is closed, controls the pump to perform a predetermined pumping operation to pump an additional amount of the liquid into the passages or to pump an additional amount of the liquid until the pressure detected by the pressure sensor reaches a predetermined pressure value; collects second pressure data generated by the pressure sensor while the shut-off device remains closed and the additional amount of the liquid is in the passages and chamber; determines a second pressure value based on the second pressure data or determines the additional amount of the liquid, and determines a dimensional characteristic of the blood passage based on a comparison of the first pressure value and the second pressure value or based on the additional amount of the liquid pumped to reach the predetermined pressure value.

A method has been conceived and is disclosed herein to determine a type of blood circuit attached to an extracorporeal blood treatment console having a pump, the circuit including a first blood passage and a second blood passage connectable to the pump and including a chamber having a gas filled region, the method comprises: pumping a liquid into the first blood passage, wherein the pumped liquid flows through the second blood passage; closing the second blood passage downstream of the chamber after the first blood passage and second blood passage fills with the liquid; sensing a first pressure of the liquid while the liquid is in the first and second blood passages, the pump is stopped and the second blood passage remains closed; after sensing the first pressure and while the second passage remains closed, pumping an additional amount of the liquid into the first blood passage; sensing a second pressure while the additional amount of liquid remains in the first and second blood passages and while the second blood passage remains closed; determining a dimensional characteristic of one of the blood passages based on the second pressure and the amount of the additional liquid.

According to a first independent aspect an extracorporeal blood treatment console is provided including at least one pump and a controller, the pump being connectable to an extracorporeal blood circuit including a blood passage having a first section connectable to a patient, a second section coupled to the pump, wherein the second section includes a chamber having an gas filled portion, a third section connected to the patient, and the controller: a.

controls the pump to pump a liquid into the first section of the blood passage; b. closes the third section or issues a prompt to close the third section, after the liquid has been pumped into the blood passage; c. receives first pressure data from the pressure sensor while the pump is stopped and the shut-off device connected to the third blood section remains closed; d.

determines a first pressure value based on the first pressure data; e. while the shut-off device is closed, controls the pump to pump an additional amount of the liquid into the blood passage; f. receives second pressure data generated by the pressure sensor while the shut-off device remains closed and the additional amount of the liquid is in the blood passage; g. determines a second pressure value based on the second pressure data, and h. determines a dimensional characteristic of the blood passage based on the second pressure value and the additional amount of the liquid.

In a second aspect according to the first aspect the additional amount of the liquid is based on a predetermined amount of pumping, and the determination of the dimensional characteristic of the blood passage is based on a comparison of the first pressure value and the second pressure value.

In a $3^{rd}$ aspect according to the $2^{nd}$ aspect the predetermined amount of pumping is achieved by pumping the liquid for a predetermined pumping displacement.

In a 4th aspect according to any of the previous aspects the determination of dimensional characteristic of the blood passage is determined based on the additional amount of the fluid pumped to cause the second pressure value to reach a predetermined pressure value.

In a 5th aspect according to any of the previous aspects the dimensional characteristic is a diameter of the blood passage.

In a 6th aspect according to any of the previous aspects the controller generates an audible or visual signal indicative of the determined dimensional characteristic.

In a 7th aspect according to the 6th aspect the audible or visual signal indicates whether the blood passage is for an adult blood circuit or a non-adult blood circuit.

In a 8th aspect according to any of the previous aspects the controller verifies whether the determined dimensional characteristic is within a predetermined range of dimensional characteristics associated with an operational setting of the console.

BRIEF DESCRIPTION OF THE DRAWINGS

The description will be made with reference to the accompanying figures of the drawings, provided by way of non-limiting example, in which.

DETAILED DESCRIPTION OF THE INVENTION

Figure 1:
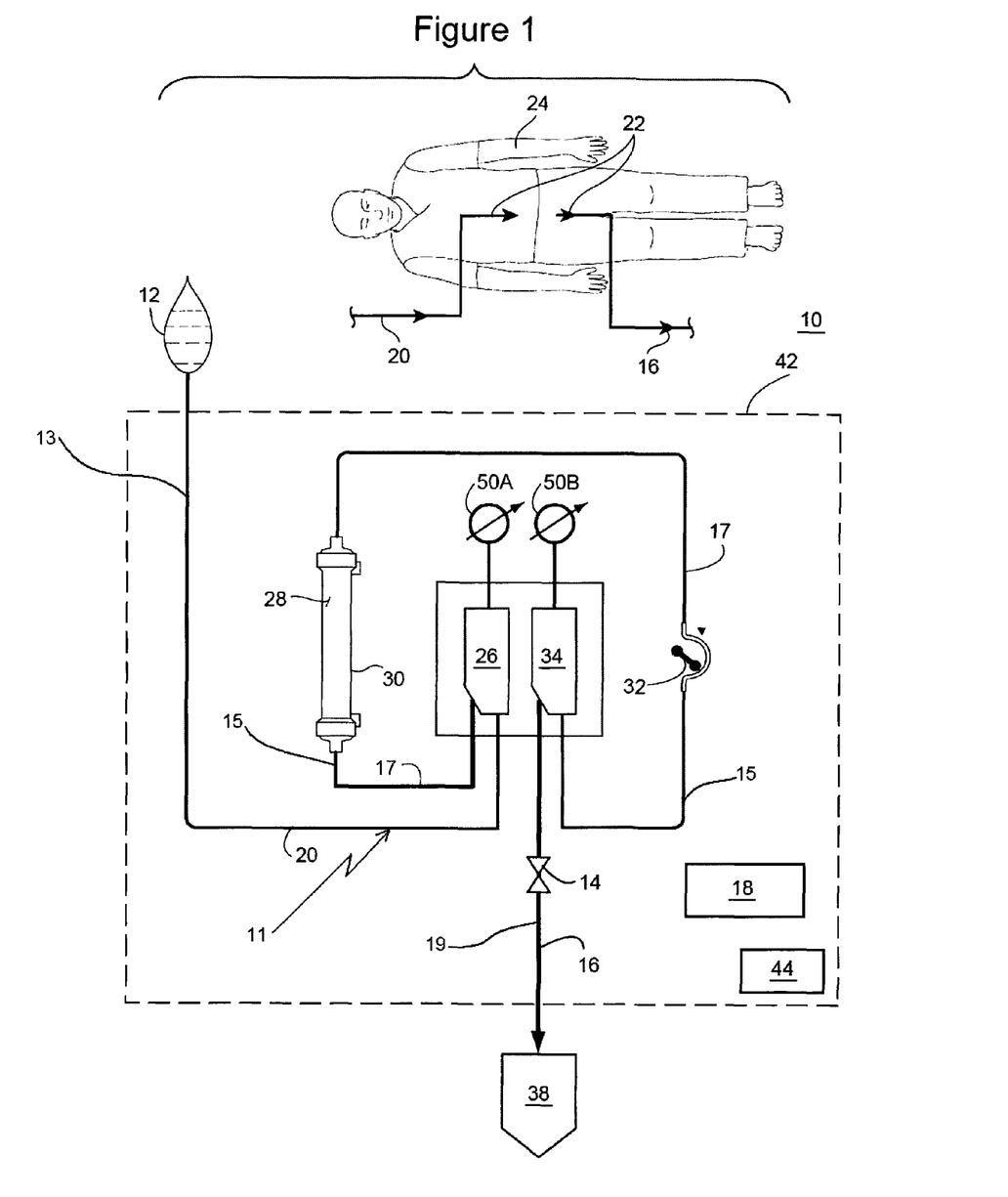
FIG. 1 is a schematic diagram of an extracorporeal blood treatment system configured to detect or verify a type of blood circuit attached to the console.

FIG. 1 shows schematically a blood treatment system 10 coupled to a priming bag 12 filled with a priming solution, such as a saline solution. The figure has been simplified to exclude components of the blood treatment system not pertinent to this description. The priming bag 12 is used to purge the passages of the blood circuit in the system of air and/or contaminates before starting blood treatment. The blood treatment system 10 is in conventional priming configuration with the exception of the shut-off device 14, such as a clamp or, valve or an occlusion device, on the blood access line 16. In addition, the program instructions for detecting the blood circuit stored in a controller 18 are not conventional.

Before blood is withdrawn from the patient into the blood treatment system 10, a nurse or other medical professional connects the priming bag 12 to the return line 20 for the blood circuit. After priming, the return line 20 is disconnected from the priming bag and connected via access devices 22 to the vascular system of the patient 24.

The return line 20 is connected to a first chamber 26 generally working as a first bubble trap 26. Priming fluid flow from the first chamber (bubble trap) through a blood line 17 to a blood chamber 28, also referred to as an arterial chamber, of a blood treatment device 30, for example a filtration unit. The blood line 17 provides a passage for blood from the blood chamber 28 to flow to a second chamber 34 generally working as a second bubble trap 34. The first and second bubble traps 26, 34 may each have an associated pressure sensor 50a, 50b. At least the second chamber 34 has one pressure sensor 50b. Each pressure sensor 50a, 50b generates data indicating a pressure in its respective bubble trap, such as a gas pressure in an upper region of the bubble trap.

The blood line 17 is coupled to a displacement (e.g. peristaltic) blood pump 32, such as a roller pump. The pump 32 moves the priming liquid through the blood lines 20, 17 to the second bubble trap 34. The priming fluid flows from the second bubble trap to a blood access line 16 and to a drain or collection bag 38. The return line 20, first bubble trap 26, blood chamber 28, blood pump line 17, second bubble trap 34 and the access line form the blood circuit, e.g., blood flow passage, through the extracorporeal blood treatment device.

After the blood treatment system 10 has been primed by filling priming liquid in all lines of at least the blood circuit, the return line 20 is disconnected from the priming bag 12 and connected to the access port to infuse treated blood from the blood circuit into the patient 24, the access line 16 is separated from the drain or collection bag 38 and connected to an access port 22 to withdraw blood from the patient to the blood circuit.

The blood circuit or portions thereof may be releasably connected to a control and pumping console 42 that includes a least one pump 32, a controller 18 and a user interface 44 such as a display and keypad. The user interface allows an operator to input operating parameters for the blood treatment and monitor the blood treatment and other processes performed by the system 10. These operating parameters, e.g., settings, may depend on whether an adult or pediatric blood circuit is to be used in the blood treatment.

The controller 18 may generally include a computer or other processor and non-transitory computer memory storing program instructions for controlling the pumps and other controllable features of the system. The computer or processor executes the program instructions to control the pumps to prime the blood circuit, regulate blood treatment and (of particular relevance to the present invention) to detect or verify the type of blood circuit attached to the console.

Figure 2:
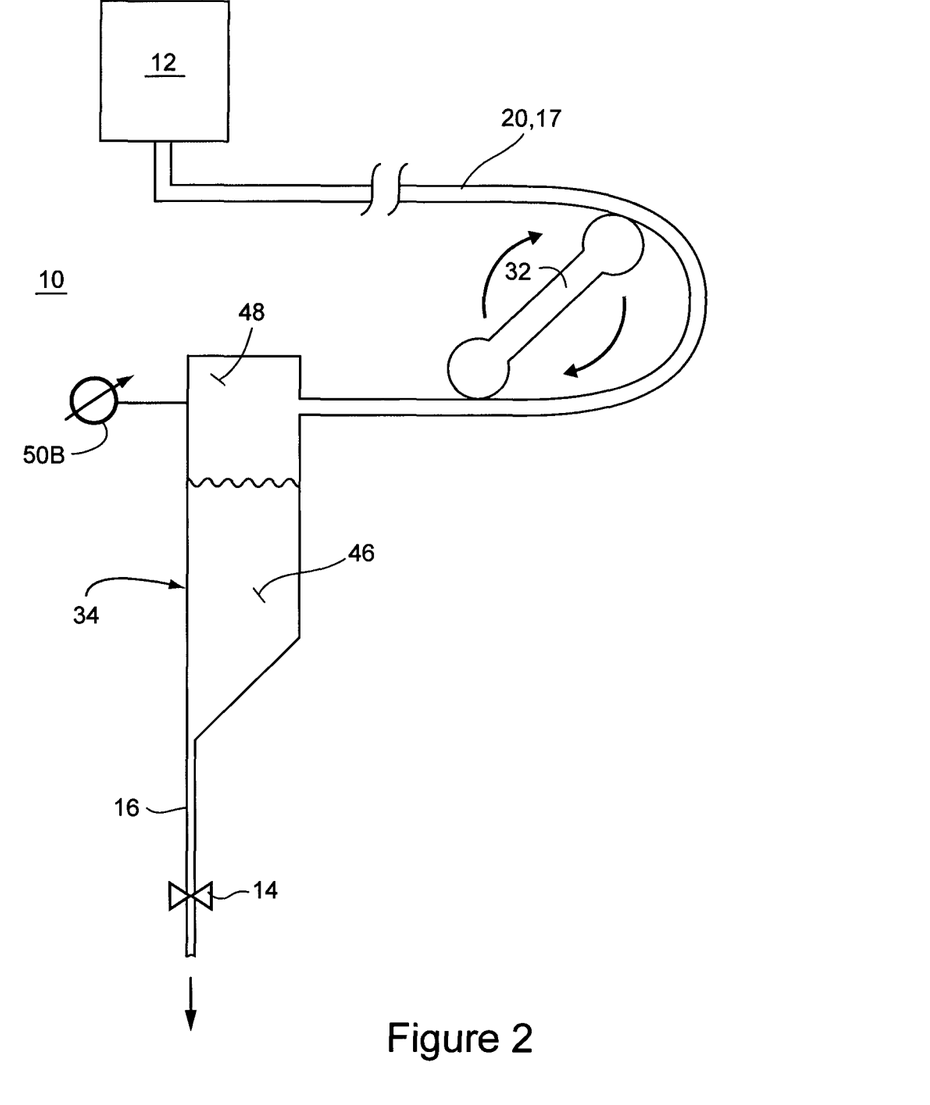
FIG. 2 is a schematic diagram of a portion of the extracorporeal blood treatment system shown in FIG. 1.

FIG. 2 is a schematic diagram of a portion of the blood treatment system 10 shown in FIG. 1. FIG. 2 illustrates an example of a bubble trap 26, 34 having a blood chamber 46 which includes an upper air or gas filled portion 48. A pressure sensor 50a, 50b is mounted to the bubble trap 26, 34 and monitors the fluid pressure in the blood chamber 46 and particularly the air filled portion 48 of that chamber.

While the shut-off device 14 is open, priming fluid drains from the blood chamber 46 and flows to a drain or collection bag 38 or other drainage collection vessel. The pump 32 is stopped and the shut-off device is closed 14 to block the drainage of priming fluid from the chamber and to retain a portion of the priming fluid in the blood circuit. The shut-off device should be closed quickly after the pump is stopped to ensure that the blood circuit is substantially filled with priming fluid, except for the gas filled region of the second bubble trap. The shut-off device may be automatically shut by the controller 18 in conjunction with the stopping of the pump 32. Alternatively, the shut-off device may be manually closed in response to an audiovisual prompt generated by the controller. After the pump is stopped and the shut-off device is closed, a first pressure level is measured by the pressure sensor 50b mounted to the second bubble trap 46.

After the first pressure level is measured and the shut-off device closed, the blood pump may pump a predetermined additional amount of priming fluid such that at least some of the additional priming fluid enters the chamber 46 of the second bubble trap 34. The pressure in the chamber 46 rises as the additional priming fluid enters the chamber because the fluid is prevented from draining due to the closed shut-off device. Assuming that the chamber 46 has a gas filled portion 48, the pressure in the chamber should rise in direct proportion to the amount of priming fluid entering the chamber.

As the priming fluid enters the chamber 46, the volume of the gas portion 48 is reduced. Boyle's Law states that for a compressible gas the product of the pressure and volume is a constant (P×V=K). Accordingly, the reduction of the volume of the gas portion 48 in the chamber should result in a proportional rise in the pressure as sensed by the pressure sensor 50b.

The volume of the gas filled portion is reduced in proportion to the amount of priming fluid entering the chamber while the shut-off device 14 is closed. The pumping may be at a predetermined rate and period to add priming fluid to the chamber while the shut-off device is closed. The amount of priming fluid added depends on the diameter of the return line 20. The short blood lines 17 may be ignored due their relatively small volume. The larger the diameter of the return line, the greater the amount of priming fluid moved with each rotation of the pump 32.

Because the amount of priming fluid added to the chamber 46 of the bubble trap 34 while the shut-off device 14 is closed depends on the diameter of the blood lines, the pressure in the chamber 46 will also depend on the diameter of the blood lines, e.g., the return line. The pressure rise in the chamber 46 indicates the diameter of the return line provided that the pumping of priming fluid into the chamber while the shut-off device is closed is controlled. In one example, the control may be to cause a predetermined pumping displacement, such as turning the pump through a half or quarter rotation or also a few degree rotation.

Figure 3:
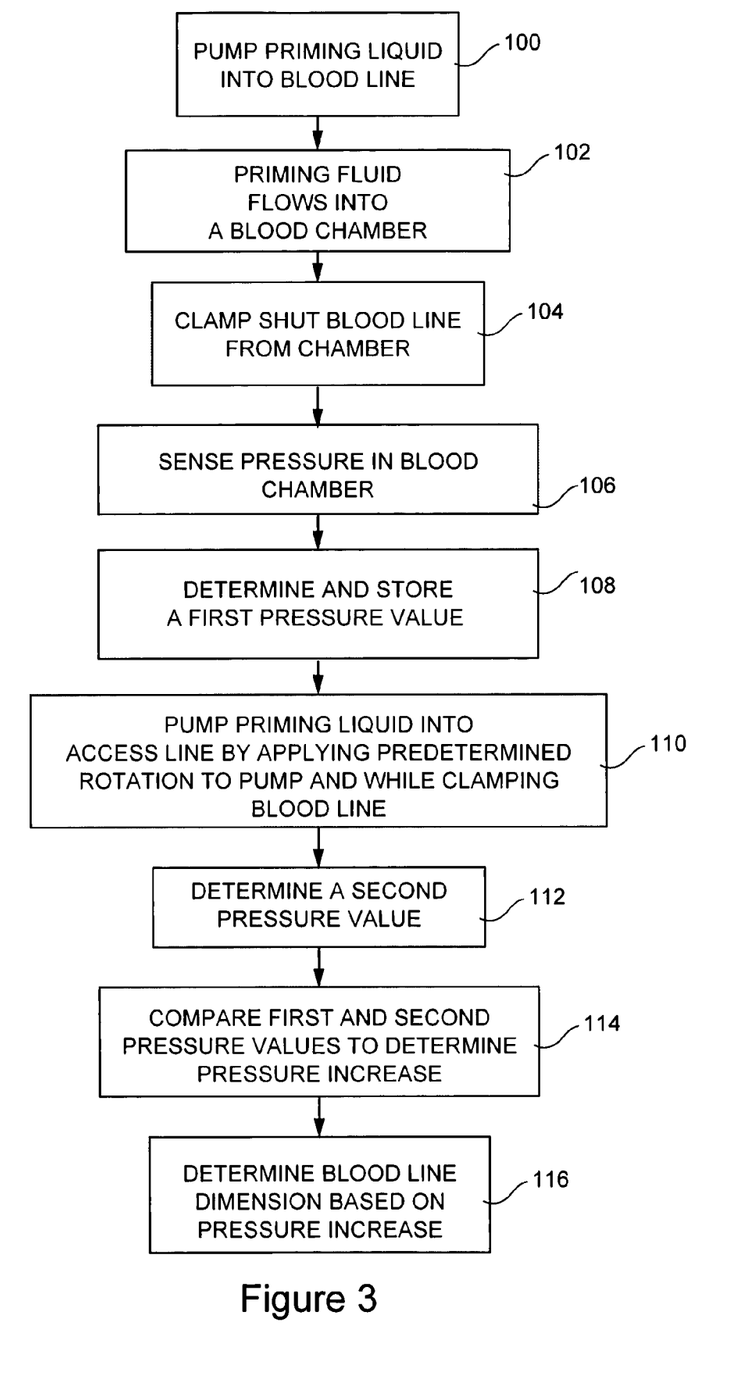
FIG. 3 is a flow chart of steps performed by a controller of the extracorporeal blood circuit for detecting or verifying a type of blood circuit attached to the console.

FIG. 3 is a flow chart showing exemplary control steps that are executed by the controller to detect or verify the type of blood circuit.

In step 100, the controller operates the blood pump 32 to pump priming liquid from a liquid source, e.g. the priming bag 12, through the return line 20, blood treatment device 30, blood pump insert line 16 and into the blood chamber 46 of the second bubble trap 34. In step 102, the priming liquid flows from the blood chamber and into and through the access line 16, and is collected in the drain or in a collection bag 38.

In step 104, the blood pump is stopped and the shut-off device shut to close the access line 16. In step 106, the controller 18 collects a first set of pressure data from a pressure sensor 50b monitoring pressure in the blood chamber 46, or a pressure in another portion of the blood circuit. Step 106 may be performed while the shut-off device is closed and the pump stopped. In step 108, the controller 18 determines and stores a first pressure value based on the first pressure data.

The first pressure level may alternatively be measured while the pump is turning and the shut-off device opened. In this alternative pressure measurement, the pump may be stopped and the shut-off device closed after the first pressure level is measured. However, the closing of the shut-off device may affect the pressure in the line and be a factor in determining the pressure differential between the first and second pressure levels.

In step 110, while the shut-off device is closed, the controller controls the blood pump 32 to pump a predetermined amount of additional priming liquid into the return line 20, bubble trap 34 and a portion of the access line 16 upstream of the shut-off device 14. The blood pump 32 is controlled to turn through a predetermined angle or number of rotations such that a predetermined amount of additional priming liquid is pumped into the blood circuit. For example, the blood pump may controlled to turn a quarter or half turn to pump additional priming fluid into the blood chamber and raise the pressure in the lines 20, 17 and second bubble trap 34.

In step 112, the controller 18 collects second pressure data generated by the pressure sensor 50b while the shut-off device 14 remains closed. The second pressure data is collection while the additional priming liquid remains in the access line, the blood treatment device and blood passage. A second pressure value is determined by the controller based on the second pressure data. The first set of pressure data may be stored in non-tangible computer memory assessable by a processor associated with the controller. The processor executes program instructions stored in the memory which cause the processor to control the pump and console to perform the steps shown in FIG. 3.

In step 114, the controller compares the first pressure value and the second pressure value to determine the pressure increase due to the additional predetermined amount of liquid added to the blood circuit in step 110. This determination may be based on whether the pressure increase is within a predetermined range corresponding to an adult blood circuit or a predetermined range corresponding to a non-adult blood circuit, such as a pediatric blood circuit.

The pressure increase is dependent on the volume of the return line, which is dependent on the diameter of the return line. The pressure increase can be used to determine the diameter of a line in the blood circuit, which indicates the type of blood circuit connected to the console. By indicating the diameter of a blood line, the pressure increase can be used by the controller to determine a dimensional characteristic of the blood passage.

Alternatively, step 110 may be performed by controlling the blood pump to pump the priming fluid until the pressure in the blood chamber 46 reaches a predetermined level. When the predetermined pressure level is reached, the controller determines the amount of pumping, such as by determining the amount of rotation of the blood pump during step 110 (or the timing of pump activation). For a small diameter return line, the pump rotation will be less to reach a predetermined pressure than the amount of pump rotation needed to increase the pressure in a large diameter a line. The amount of pump rotation needed to reach a predetermine pressure rise is an alternative method to determine the dimensional characteristic of the blood access line.

The types of releasable blood circuits which may be attached to the console may include an adult circuit suitable for performing treatments on adult patients (large diameter blood line for adults), and a pediatric circuit suitable for performing treatment on child patients (pediatric blood line are relatively small diameter tubes). These two types of blood circuits, for adults and children, differ in the internal diameter of the access line. The diameter of the access line is greater in blood circuits for adults and is smaller for pediatric blood circuits.

In setting-up of the console for an extracorporeal treatment for a child in general, the settings or desired values of the flow rates of the blood pump and others pumps on the console for pumping the various fluids to be used in the blood treatment (blood flow rate, anticoagulant flow rate, dialysis fluid flow rate, replacement fluid flow rate, infusion fluid flow rate etc.) are lower than the corresponding settings or desired values for a treatment destined for an adult.

The steps show in FIG. 3 may be used by the controller to automatically determine and recognize the type of blood circuit attached to the console. Alternatively, the steps may be used by the controller to verify that the type of blood circuit mounted to the console is the same blood circuit type which the operated identified while inputting the parameters to the user interface 44.

If the detection or verification process shown in FIG. 3 recognizes that the blood circuit matches the adult/child selection made by the operator, no alert (audible or visual) to the operator is generated by the controller. If the detection verification process determines that the blood circuit does not match the type of blood circuit selected by the operator using the user interface, the controller may operates an automatic intervention, e.g. a stop of the priming procedure or issue an alert to the user.

The detection and verification process herein described enables the controller to recognize whether an extracorporeal blood circuit of the disposable type for adults has been mounted on the treatment apparatus in the place of one for children, and vice versa. In this way an accidental exchange of circuits, which could cause damage to a patient, can be avoided.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An extracorporeal blood treatment console comprising:
   at least one pump connectable to an extracorporeal blood circuit including a blood passage having a first section connectable to a patient, a second section coupled to the pump, wherein the second section includes a chamber having a gas filled portion, a third section connected to the patient and a sensor for sensing a parameter data of the extracorporeal blood circuit, and
   a controller being configured to perform the following steps:
   a. controlling the pump to pump a liquid into the first section of the blood passage;
   b. closing the third section or issuing a prompt to close the third section, after the liquid has been pumped into the blood passage;
   c. receiving a first parameter data from the sensor, said first parameter data being chosen in a group comprising a pressure data from a pressure sensor, a fluid level data from a level sensor, a volume data from a capacitive sensor, a shut-off device connected to the third blood section remaining closed, while the pump is stopped;
   d. determining either a first pressure value based on the first parameter data or a first level value based on the first parameter data or a first volume value based on the first parameter data, the pressure value being a pressure value of the fluid in the blood passage or of the gas in the gas filled portion, the level value being a level value of the fluid in the chamber, the volume value being the value of the gas filled portion or of the liquid filled portion of the chamber;
   e. while the shut-off device is closed, controlling the pump to pump an amount of the liquid into the blood passage;
   f. receiving a second parameter data from the sensor, said second parameter data being chosen in a group comprising a pressure data generated by the pressure sensor or a fluid level data from the level sensor, a volume data from the capacitive sensor, while the shut-off device remains closed and the modified amount of the liquid is in the blood passage;
   g. determining either a second pressure value based on the second parameter data or a second level value based on the first parameter data or a first volume value based on the first parameter data, and
   h. determining a dimensional characteristic of the blood passage based on the second pressure value or the second level value and/or the second volume value and the modified amount of the liquid.

2. The extracorporeal blood treatment console of claim 1 wherein the modified amount of the liquid is based on a predetermined amount of pumping of liquid into the chamber or away from the chamber, and the determination of the dimensional characteristic of the blood passage is based on a comparison of the first value and/or the second value and a prefixed threshold.

3. The extracorporeal blood treatment console of claim 2 wherein the predetermined amount of pumping is achieved by pumping the liquid for a predetermined pumping displacement, before and after the pumping of the predetermined amount, the pump substantially occluding a portion of the second section avoiding fluid passage between the second section and the first section.

4. The extracorporeal blood treatment console of claim 1 wherein the determination of dimensional characteristic of the blood passage is determined based on the modified amount of the fluid pumped to cause the second value to reach a predetermined value.

5. The extracorporeal blood treatment console of claim 1 wherein the dimensional characteristic is a diameter or a transversal cross section or a resistance to fluid passage of the blood passage.

6. The extracorporeal blood treatment console of claim 1 wherein the controller generates an audible or visual signal indicative of the determined dimensional characteristic.

7. The extracorporeal blood treatment console of claim 6 wherein the audible or visual signal indicates whether the blood passage is for an adult blood circuit or a non-adult blood circuit.

8. The extracorporeal blood treatment console of claim 1 wherein the controller verifies whether the determined dimensional characteristic is within a predetermined range of dimensional characteristics associated with an operational setting of the console.

9. The extracorporeal blood treatment console of claim 1 wherein a portion of the extracorporeal blood circuit is hydraulically isolated from a remaining portion of the extracorporeal blood circuit when determining the first and the second values, said portion including a first tract between the pump and the chamber, and a second tract between the chamber and the shut off device.

10. The extracorporeal blood treatment console of claim 1 wherein the first value and the second value are pressure values of the gas filled portion of the chamber.

11. The extracorporeal blood treatment console of claim 1 wherein the pump is a peristaltic pump and the controller is configured to control the pump to perform a rotation of less then 180 degrees.

12. The extracorporeal blood treatment console of claim 1 wherein the second section includes a first chamber, a filtration unit to filter blood, and a second chamber, the pump being interposed between one of the chambers and the filtration unit, the filtration unit being interposed between the pump and the other chamber.

13. The extracorporeal blood treatment console of claim 9 wherein the first tract between the pump and the chamber and the second tract between the chamber and the shut off device are filled with liquid when performing the first and second value determinations, the chamber being partly filled with liquid, partly filled with gas.

14. An apparatus for extracorporeal blood treatment comprising:
   a blood circuit including a blood passage having a blood return section adapted to convey treated blood to be infused in a mammalian patient, a blood pump section coupled to a blood chamber having a gas filled region, and a blood access section adapted to receive blood withdrawn from the patient;
   a pump associated with the extracorporeal blood treatment console and adapted to connect to the blood pump section of the blood passage;
   a pressure sensor generating pressure data indicative of a pressure in the blood passage or the blood chamber; and
   a controller configured to:
      a. control the pump to pump a liquid into the blood passage;
      b. close the blood passage downstream of the blood chamber or issue a prompt to close the blood passage downstream of the blood chamber;
      c. receive a first set of the pressure data while the pump is stopped and after the closure of the blood passage;
      d. determine and store a first pressure value based on the first set of the pressure data;
      e. while the blood passage remains closed, control the pump to perform a predetermined pumping operation to pump an additional amount of the liquid into the blood passage or to pump an additional amount of the liquid until the pressure detected by the pressure sensor reaches a predetermined pressure value;
      f. determine a second pressure value based on a second set of the pressure data collected during step (e) or determine the additional amount of the liquid; and
      g. determine a dimensional characteristic of the blood passage based on the first pressure value and the second pressure value or based on the additional amount of the liquid pumped to reach the predetermined pressure value.

15. The apparatus of claim 14 wherein the dimensional characteristic is a diameter of the blood passage.

16. The apparatus of claim 14 wherein the controller generates an audible or visual signal indicative of whether the blood passage is for an adult blood circuit or a non-adult blood circuit.

17. A method to determine a type of blood circuit attached to an extracorporeal blood treatment console having a pump, the circuit including a blood passage and a chamber having a gas filled region and in fluid communication with the blood passage, the method comprising:
   pumping a liquid into the blood passage;
   closing the blood passage downstream of the chamber after the liquid is pumped into the blood passage;
   sensing a first pressure of the liquid or chamber while the liquid is in the blood passage, the pump is stopped and the passage remains closed;
   after sensing the first pressure and while the passage remains closed, pumping an additional amount of the liquid into the blood passage;
   sensing a second pressure while the additional amount of liquid remains in the blood passage and chamber, and while the blood passage remains closed; and
   determining a dimensional characteristic of the blood passages based on at least one of the second pressure and the amount of the additional liquid.

18. The method of claim 17 wherein the additional amount of liquid is pumped until the second pressure reaches a predetermined pressure value, and the determination of the dimensional characteristic is based on a determination of the volume of the additional amount of the liquid.

19. The method of claim 17 wherein the additional amount of liquid is pumped for a predetermined pumping displacement, and a comparison is made of the first and second pressures to determine the dimensional characteristic.

20. The method of claim 17 wherein the pumping is at the predetermined pumping rate and for a predetermined pumping period.

* * * * *